United States Patent [19]
Li et al.

[11] Patent Number: 5,914,410
[45] Date of Patent: Jun. 22, 1999

[54] INTERMEDIATES FOR ANNONACEOUS ACETOGENINS

[75] Inventors: Keqiang Li, St. Paul; Faith M. Uckun, White Bear Lake, both of Minn.

[73] Assignee: Wayne Hughes Institute, Roseville, Minn.

[21] Appl. No.: 09/009,057

[22] Filed: Jan. 20, 1998

[51] Int. Cl.$^6$ .................. C07D 407/04; C07D 307/12
[52] U.S. Cl. ........................... 549/472; 549/502
[58] Field of Search ...................... 549/472, 502

[56] References Cited

PUBLICATIONS

Jolad, S.D., Uvaricin, a New Antitumor Agent from Uvaria accuminata (Annonaceae), J. Org. Chem., 1982, 47, 3151–53.

Hanson, R.M.; Sharpless, K.B. Procedure for the Catalytic Asymmetric Epoxidation of Allylic Alcohols in the Presence of Molecular Sieves, J. Org. Chem., 1986, 51, 1922–25.

Abushanab, E; et al., The Chemistry of L–Ascorbic and D–Isoascorbic Acids. 1. The Preparation of Chiral Butanetriols and –tetrols, J. Org. Chem., 1988, 53, 2602–08.

Krief, A.; et al., Stereoselective Synthesis of Methyl (1R) Trans – and(1R) Cis – Hemicaronaldehydesfrom Natural Tartaric Acid Application to the Synthesis of S–Bioallethrin and Deltamethrin Insecticides, Tetrahedron, 1989, 45, 30390–52.

Alkofahl, A; et al., Gigantecin: A Novel Antimitotic and Cytotoxic Acetogenin, With Nonadjacent Tetrahydrofuran Rings, from Goniothalamus Giganteus (Annonaceae), Experiments, 1990, 46, 539–41.

Bertrand, P.; Gesson, J–P., Approach to the Synthesis of Annonaceous Acetogenins From D–Glucose, Tetrahedron Letters, 1992, 33, 5177–80.

Harmange, J–C.; et al., Stereocontrolled Synthesis of 2.5–Linked Monotetrahydrofuran Units of Acetogenins, Tetrahedron Letters, 1992, 33, 5749–52.

Gu, Z.; et al., Gonionenin: A New Cytotoxic Annonaceous Acetogenin From Goniothalamus Giganteus and the conversion of Mono–THF Acetogenins to Bis–THF Acetogenins, J. Org. Chem., 1994, 59, 3472–79.

Koert, W.; et al., A Convergent Synthesis of 2,5–Trans––Linked Oligo (Terahydrofuran)s: Potential Building Blocks for a Polyether Helix With Ion Channel Activity, Angew. Chem. Int. Ed. Engl., 1994, 33, 1180–82.

Koert, U., Stereoselective Synthesis of Oligo–Tetrahydrofurans, Synthesis, Feb. 1995, 115–32.

Makabe H.,; et al., Total Synthesis of Solamin and Reticulatacin, J. Chem. Soc. Perkin Trans. 1, 1994, 1975–81.

Yao, Z–J.; Wu, Y–L., Total Synthesis of (10E, 15R, 16S, 19S, 20S, 34R)—Corossoline, Tetrahedron Letters, 1994, 35, 157–60.

Yao, Z–J.; Wu, Y–L.,Synthetic Studies Toward Mono–THF Annonaceous Acetogenins: A diastereoselective and Convergent Approach to Corossolone and (10RS)—Corossoline, J. Org. Chem., 1995, 60, 1170–76.

Figadere, B., Synthees of Acetogenins of Annonaceae: A New Class of Bioactive Polyketides, Acc. Chem. Res., 1995, 28, 359–65.

Hoye, T.R.; Ye, Z., Highly Efficient Synthesis of the Potent Antitumor Annaceous Acetogenin (+)—Parviflorin, J. Am. Chem. Soc., 1996, 118, 1801–02.

Zeng, L.; et al., Recent Advances in Annonaceous Acetogenins, Natural Product Reports, 1996, 275–306.

Figadere, B.; et al., Replicative Chirons: Stereoselective Synthesis of Oligo–Tetrahydrofuranic Lactones Via C–Glycosylation With [(Trimethylsily)oxy]furan, J. Org. Chem. 1997, 62, 3428–29.

Gu, Z–M,; et al., Chapter Eleven—Annonaceous Acetogenins, Phytochemistry of MedicinalPlants, Amason et al., Plenum Press, N.Y., 1995, 249–310.

*Primary Examiner*—Bernard Dentz
*Attorney, Agent, or Firm*—Merchant & Gould

[57] ABSTRACT

Novel tetrahydrofuran-epoxide compounds are described as intermediates for the preparation of non-adjacent bis-THF-acetogenins of pharmaceutical interest. Also described is a novel stereocontrolled synthesis for preparing such intermediates starting with commercially available enantiomers of glycidyl benzylether.

13 Claims, No Drawings

INTERMEDIATES FOR ANNONACEOUS ACETOGENINS

FIELD OF THE INVENTION

The invention relates to novel intermediates, particularly a tetrahydrofuran (THF) epoxide prepared according to a stereocontrolled method which can be used to prepare therapeutically active mono-THF and bis-THF acetogenins.

BACKGROUND OF THE INVENTION

Since the first discovery of uvaricin in 1982[1], more than 220 annonaceous acetogenins have been reported. Considerable attention has been paid to this class of naturally occurring polyketide-derived fatty acids due to their pleiotropic biological activities[2], including their immunosuppressive and anti-neoplastic properties. Acetogenins are optically pure compounds frequently containing 1–3 tetrahydrofliran (THF) rings in the center of a long hydrocarbon chain. The stereochemistry of the THF rings may affect the activity of acetogenins since it has been noticed that different stereoisomers of acetogenins display strikingly different biological activity profiles. However, very little is known about the structure-activity relationships contributing to these differences.

[1] Jolad, S. D.; Hoffman, J. J.; Schram, K. H.; Tempesta, M. S.; Kriek, G. R.; Bates, R. B.; Cole, J. R. *J. Org. Chem.* 1982, 47, 3151.
[2] Zeng, L.; Ye, Q.; Oberlies, N. H.; Shi, G.; Gu, Z. -M.; He, K.; McLaughlin, J. L. *Natural Product Reports,* 1996, 275 and references cited therein.

Earlier reports described schemes for total synthesis of mono-THF and bis-THF acetogenins.[3] However, very few synthetic strategies yielding the central core THF-unit of mono-THF containing acetogenins are stereoselective and therefore require chromatographic separation of the key intermediates.[4] We have now developed an efficient and stereocontrolled approach to synthesize the central core THF-unit of mono-THF containing acetogenins which allows each stereogenic center around the THF ring to be controlled.

[3] a) Figadere, B.; Peyrat, J. -F.; Cave, A. *J. Org. Chem.* 1997, 62, 3248 and references cited therein. b) Hoye, T. R.; Ye, Z. *J. Am. Chem. Soc.* 1996, 118, 180 1. c) Figadere, B. *Acc. Chem. Res.* 1995, 28, 359 and references cited therein.
[4] a) Gesson, J. -P.; Bertrand, P. *Tetrahedron Lett.* 1992, 33, 5177. b) Harmange, J. -C.; Figadere, B. Cave, A. *Tetrahedron Lett.* 1992, 33, 5749. c) Makabe, H.; Tanaks, A.; Oritani, T. *J. Chem. Soc. Perkin Trans. I,* 1994,1975. d) Wu, Y. -L.; Yao, Z. -J. *Tetrahedron Lett.* 1994, 35, 157. e) Wu, Y. -L.; Yao, Z. -J. *J. Org. Chem.* 1995, 60, 1170.

SUMMARY OF THE INVENTION

Accordingly the present invention is directed to a stereocontrolled synthesis of a central core tetrahydrofuran (THF)-unit of mono-THF containing acetogenins. The invention also includes novel intermediates which are key in the synthesis of the therapeutically active mono-THF acetogenins, particularly, for example, corossolone, and (10RS) corossoline.

The present invention includes as a novel intermediate for the synthesis of the above acetogenins a stereoisomeric compound of the formula

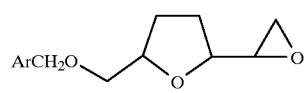

I.

wherein Ar is phenyl or substituted phenyl.

A particular compound of choice in this case is the compound of the formula I where Ar is phenyl.

Another novel intermediate of the present invention is a stereoisomeric compound of the formula

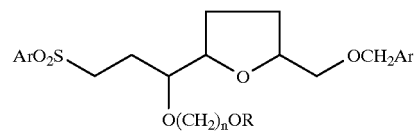

II.

wherein Ar is phenyl or substituted phenyl, R is lower acetyl, and n is 1 or 2. The preferred compound in this instance is the compound of the formula II where Ar is phenyl; R is methyl and n is 1.

The present invention also includes a process for preparing the intermediate of the formula I which includes the steps of:

(a) reacting a stereoisomeric compound of the formula

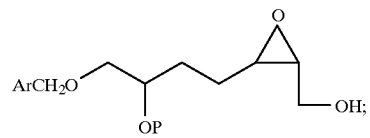

III wherein P is an acid labile protective group with an aromatic carboxylic acid halide or anhydride, or an aromatic sulfonyl halide to form a stereoisomeric compound of the formula

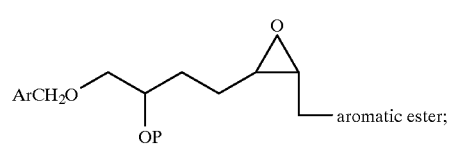

IV (b) reacting the resulting aromatic ester of formula IV with an acidic resin in an alcohol solvent to afford a stereoisomeric compound of the formula

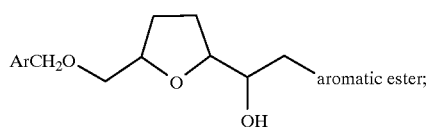

V (c) reacting the product of step (b) of formula V with a methane sulfonyl halide or aryl-sulfonyl halide followed by an alkali metal alkoxide or carbonate in an alcohol solvent to afford the product of the above formula I.

DETAILED DESCRIPTION

The following terms used throughout the present application have the following meanings:

The term "stereoisomeric" compound means the compound depicted by its respective formula existing in any of 8 possible optical isomers. The compounds of Formulae I through V have three asymmetric carbon atoms or chiral centers and each center containing the asymmetric carbon atoms connected to four different groups exist either in the R configuration or S configuration.

By way of illustration the asymmetric carbon atoms or chiral centers of the compounds of Formula I and II are designed with an asterisk as follows:

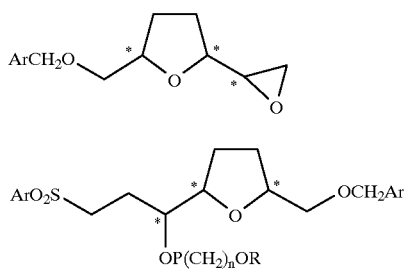

The term "Ar" stands for an aromatic group and is particularly a phenyl or a substituted phenyl group wherein the substituents are those that are typically used in organic chemistry or an aromatic ring such as, for example, alkyl, alkoxy, halo or nitro.

The term "alkyl" denotes a straight or branched hydrocarbon chain and with the term "lower" includes such straight or branched hydrocarbon chain having from 1 to 7 carbon atoms. As a preferred embodiment, chains from 1 to 4 carbon atoms are included. These include as examples, methyl, ethyl, propyl, isopropyl, butyl, secondary butyl, t-butyl, and the like.

The term "alkoxy" refers to an alkyl moiety connected to an oxygen atom depicted by the formula OR, where R is an alkyl chain as defined above. Preferred alkoxy groups include methoxy, ethoxy, propoxy, butoxy, and the corresponding branched chain alkoxy groups of the propoxy and butoxy groups.

The term "halo" includes the halogen family and particularly fluoro, chloro, bromo, and iodo. A preferred halo substituent is chloro.

The term "acid labile protective" group means any group capable of protecting a hydroxyl group and capable of being easily removed under acidic conditions without affecting other functional groups in the compound. These include groups having an oxygen atom located off a carbon atom attached to the oxygen atom of the hydroxy group, e.g.

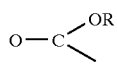

Such groups include, for example, methoxymethyl, 1-ethoxyethyl, tetrahydropyranyl and the like.

The synthesis of the novel intermediates of the present invention by a stereocontrolled method is illustrated by way of example in Schemes 1 and 2 and begin with a commercially available glycidyl benzyl ether, which is commercially available in both enantiomeric forms. Thus the synthesis shown in the schemes and described below are for the synthesis of a particular stereoisomer but the synthesis can be used to prepare all possible stereoisomers.

The epoxide, for example, (S-glycidyl benzylether) is first opened with allyl magnesium bromide using a cuprous halide catalyst, particularly, for example, cuprous bromide to provide a single regioisomer of homoallylic alcohol 1. The reaction is carried out in tetrahydrofuran as a solvent at preferably 0° C.

The hydroxyl group is then protected as the corresponding ethoxy ethyl ether by known methods, for example, an acid medium in methylene chloride solvent, and the terminal double bond is transformed to the aldehyde 2 under oxidative cleavage conditions. By way of example, the oxidation may be carried out with osmium tetroxide catalyst, N-methyl morpholine-N-oxide (NMO), then sodium periodate, $NaIO_4$ in an aqueous tetrahydrofuran medium. The aldehyde is converted to the pure (E)-α-β-unsaturated ester 3 via the Wittig-Horner reaction (as described in Krief, A.; Dumont, W.; Lecomte, P. Tetrahedron 1989, 45, 3039). The ester group is then reduced to the corresponding allylic alcohol using diisobutylaluminum hydride. Sharpless asymmetric epoxidation (as described in Hanson, R. M.; Sharpless, K. B. J. Org Chem. 1986, 51, 1922) using (L)-(+)-diisopropyl tartrate provides the corresponding epoxy alcohol 5 as the only diastereomer which can be detected by NMR spectroscopy. The hydroxy group is then converted to a (p)-nitrobenzoate 6 by treating a hydroxyl compound with a p-nitrobenzoylchloride, in the presence of triethylamine and methylene chloride solvent. The next step, one of the key steps in the overall process, is the one-step removal of the epoxy ethyl ether protective group as well as ring-closing to the tetrahydrofuran compound 7 as a single isomer. This step is carried out by using an acidic resin, particularly a Dowex resin, in methanol. Epoxide formation is then accomplished by first transforming the secondary hydroxyl group into a mesylate or tosylate by treating compound 7 with methane sulfonyl chloride or p-toluenesulfonyl chloride in the presence of triethylamine in methylene chloride solvent at about 0° C. The intermediary benzoate-mesylate compound is then treated with an alkali metal alkoxide or in an alcohol solvent, particularly, for example, sodium methoxide or potassium carbonate in methanol to yield the THF-epoxide compound 8, which is the preferred compound of the novel intermediates of formula I of the present invention.

Scheme 1

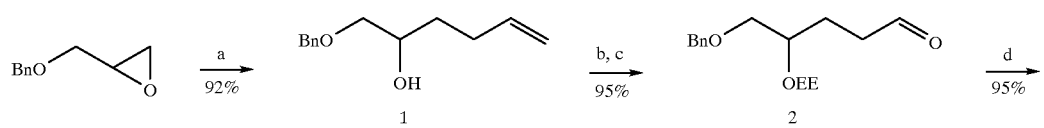

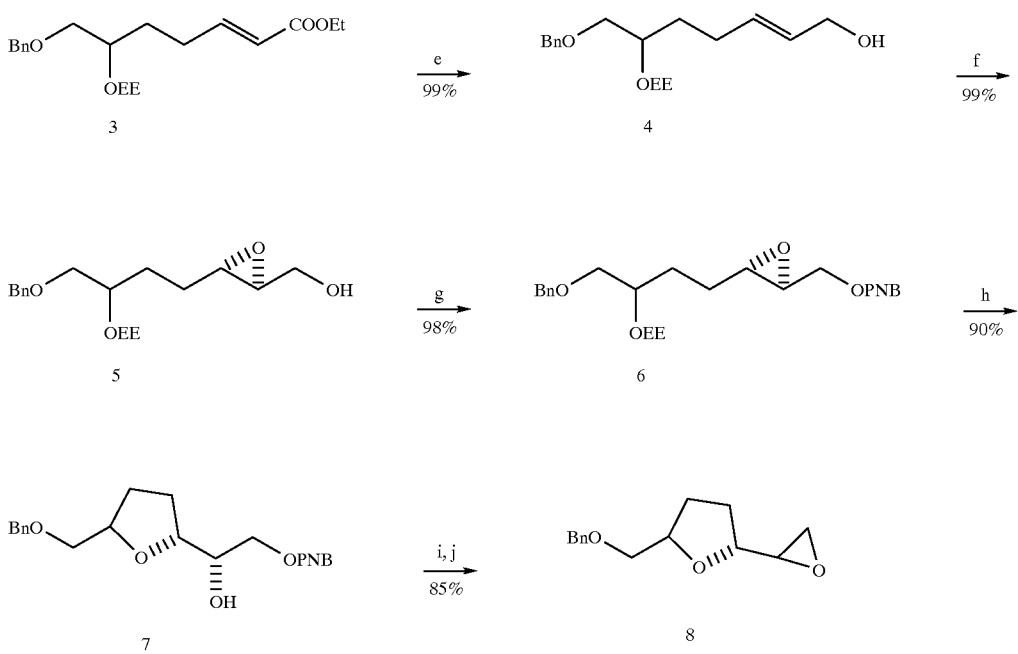

<sup>a</sup>Conditions: (a) AllylMgBr, CuBr (cat.), THF, 0° C.; (b) EVE, H⁺, CH₂Cl₂; (c) OsO₄ (cat.), NMO, then NaIO₄, THF—H₂O; (d) EtOCOCH₂P(O)(OEt)₂, NaH, DME-benzene, 0° C.; (e) DIBAL, CH₂Cl₂, -78° C.; (f) L-(+)-DIPT, Ti(OPr-i)₄, TBHP, CH₂Cl₂, -25° C.; (g) PNBCl, TEA, CH₂Cl₂; (h) Dowex-50, MeOH; (i) MsCl TEA, CH₂Cl₂, 0° C.; (j) NaOMe, MeOH, 0° C.

The novel intermediate of formula I, and particularly compound 8, is used as a key intermediate as the epoxide can be easily opened by different nucleophiles to lead to structures with a fixed stereochemical relationship around the THF-ring unit. For example, as shown in Scheme 2, compounds 9 and 10 have been prepared using undecylmagnesium bromide and methyl phenyl sulfone as nucleophiles. Compound 10 represents the preferred embodiment of the novel intermediates of formula II.

By way of example, the transformation of compound 8 to 9 takes place by treating 8 with undecylmagnesium bromide in tetrahydrofuran using a cuprous halide such as, for example, cuprous bromide at about 0° C. The hydroxyl group is then protected with a methoxy methyl group (MOM).

Conversion of compound 8 to compound 10 is also illustrated in Scheme 2 to take place in a two-step synthesis.

Scheme 2

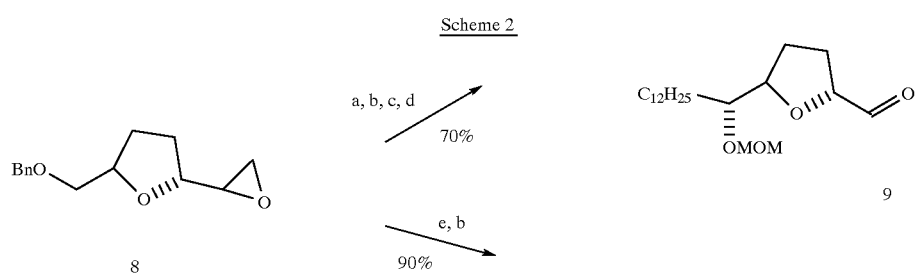

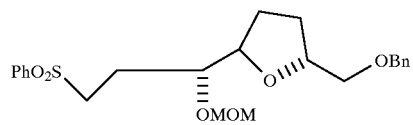

10

<sup>a</sup>Conditions: (a) $C_{11}H_{23}MgBr$, CuBr (cat.), THF, $0°C$.; (b) MOMCl, DIPEA, $CH_2Cl_2$; (c) $H_2$, Pd/C, EtOAc; (e) $(COCl)_2$, DMSO, TEA, $CH_2Cl_2$, $-78°C$.; (e) methyl phenyl sulfone BuLi, $BF_3—OEt_2$, THF, $-78°C$.

Compound 9 is the key intermediate used in the total synthesis of corossolone and corossoline (as described in Wu, Y. -L; Yao, Z. -J. *J. Org Chem.* 1995, 60, 1170).

Thus, for example, stereospecific compound 9 prepared by the method of the present invention may be used directly in the synthesis of corossolone as reported by Wu, id., and as shown in Schemes 3, 4, 5 and 6. Compound 9 as prepared by the present invention eliminates the need for separating the different isomers formed in the synthesis shown by Wu, id.

Compound 9 of the present invention where the hydroxyl group is protected by a tertiary-butyldimethyl silyl group (TBS or TBDMS) is propargylated by treatment with the enantiomerically pure allenylboronic ester, 2-allenyl-1,3-dioxa-2-borolane-(4S,5S)-dicarboxylic acid bis(1'-methylethyl) ester, prepared from an allenylboric acid and diisopropyl D-tartrate in the presence of powdered 4 Å molecular sieves. The reagent-controlled asymmetric propargylation is performed at $-78°$ C. for 24 h and gives a stereoselective product. The THF segment 13 with the desired chiral centers is obtained after silylation of homopropargyl alcohol 12 (Scheme 1).

The remaining part of the synthesis is illustrated by schemes 4, 5 and 6 and is carried out as described by Wu, id.

Scheme 3

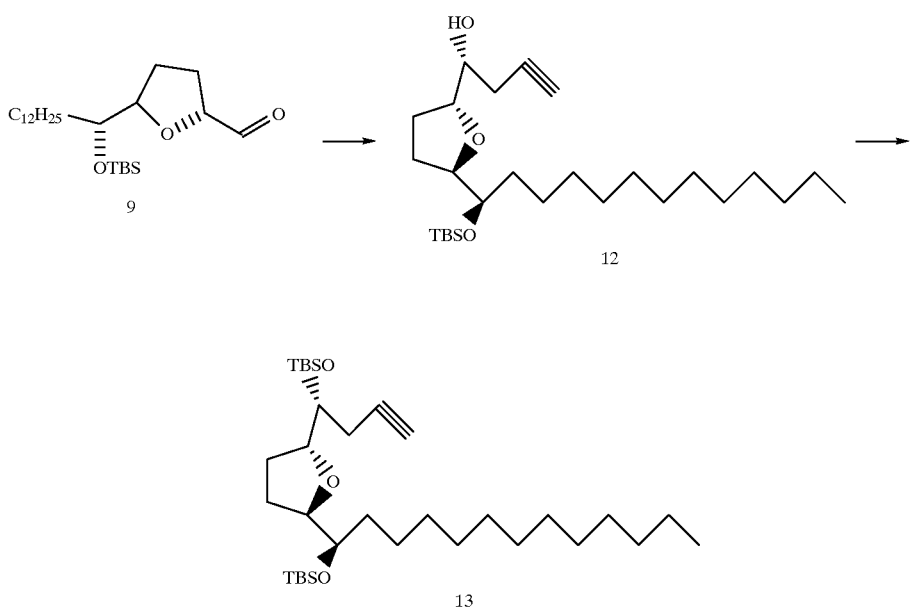

5,914,410
9                                                                                    10
Scheme 4
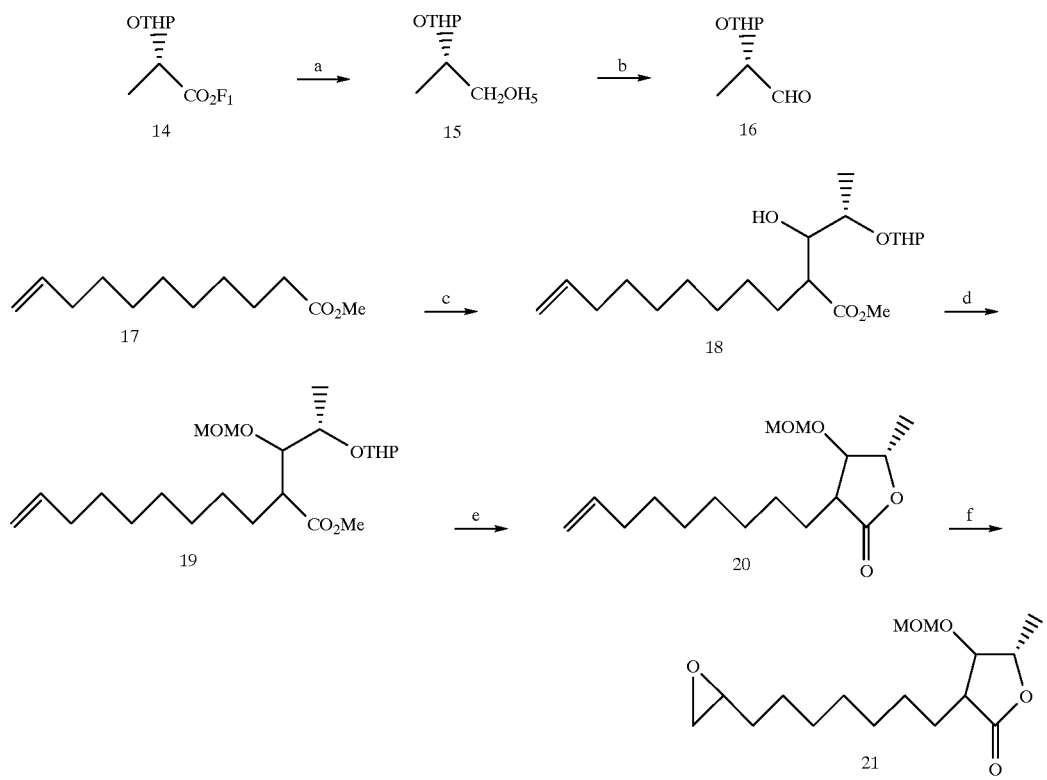
Scheme 5
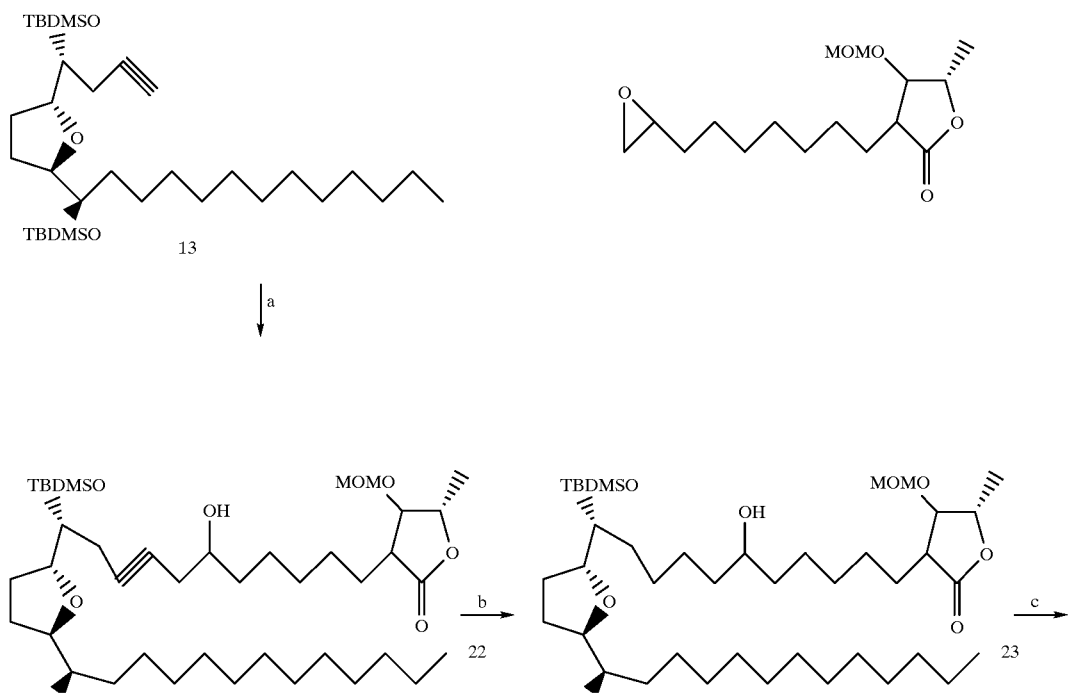

Scheme 6

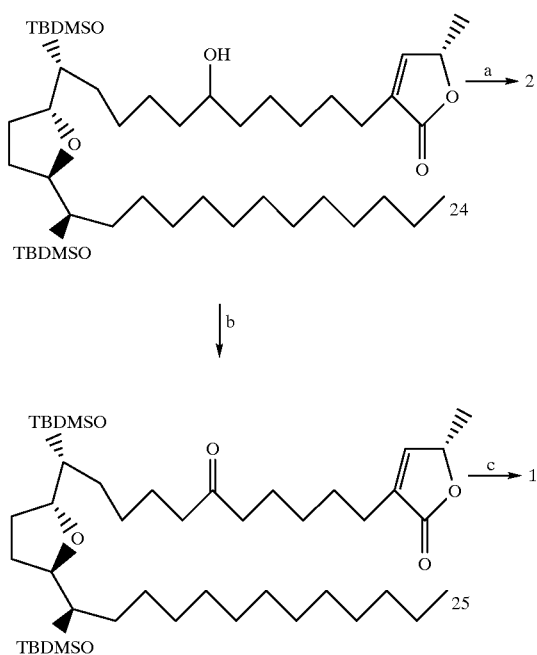

In addition, the use of intermediates 9 and 10 through coupling of these compounds may be used to prepare non-adjacent bis-THF acetogenins.

Thus, the present invention provides an efficient procedure for the stereocontrolled synthesis of THF-epoxide. This synthetic approach offers several advantages over previously described strategies. First, both enantiomers of glycidyl benzyl ether are commercially available and the stereochemical outcome in the Sharpless asymmetric epoxidation step can be selected by the use of either enantiomer of diisopropyl tartrate. Furthermore, the stereochemical outcome for the final epoxidation can also be varied by derivatizing either the primary or the secondary hydroxyl group into a leaving group. This approach can yield 8 stereoisomeric THF-epoxides and thereby provide the opportunity to generate large chemical libraries of mono-THF containing acetogenins.

EXAMPLES

Proton nuclear magnetic resonance ($^1$H-NMR) spectra were recorded at 300 MHz (Varian-300). Carbon-13 magnetic resonance ($^{13}$C-NMR) were recorded at 75.5 MHz (Varian-300). Chemical shifts are reported in parts per million (ppm) upfield from an internal reference of tetramethylsilane and coupling constants (J values) are reported in hertz (Hz). The data are reported as follows: chemical shift; number of protons; multiplicity (s—singlet, d=doublet, t=triplet, q=quartet, dd=doublet of doublets, etc.); coupling constants. Unresolved resonances and resonances complicated by non-first order splitting are reported as multiplet (m) or broadened (br), as appropriate.

All moisture-sensitive reactions were performed in oven-dried glassware under a nitrogen atmosphere maintained by rubber septa. Moisture-sensitive reagents were transferred using standard syringe and cannulation techniques.

Ethyl ether and tetrahydrofuran were distilled from sodium/benzophenone ketyl immediately prior to use. Dichloromethane was distilled from calcium hydride and used immediately. Organic amines were distilled from calcium hydride and stored over potassium hydroxide.

Flash column chromatography was performed using Baker 40 µm silica gel. For binary solvent systems, the proportion of solvents is given as volume/volume ratio.

Example 1

(2R)-1-Benyzl-5-penten-1,2-diol

To a suspension of copper bromide (700 mg) in dry THF (150 mL) at 0° C. was added dropwise allylmagnesium bromide (12.2 mL, 2.0 M solution in THF, 24.4 mmole) under nitrogen and the mixture was stirred at 0° C. for 5 min. (S)-glycidyl benzyl ether (2.0 g, 12.2 mmole) in dry TEF (10 mL) was then added dropwise and the resulting mixture was stirred at 0° C. for 1 h and quenched with saturated ammonium chloride (50 mL). The organic layer was separated from the aqueous layer and the aqueous layer was extracted with ethyl ether (2×50 mL). The combined organic extracts were washed with brine, dried over anhydrous magnesium sulfate, and concentrated using rotatory evaporation. The oily residue was purified by flash column chromatography (hexane/EtOAc=10/1) to yield 2.3 g (92%) of the desired product as a colorless oil.

$^1$H-NMR (CDCl$_3$, 300 MHz) δ: 1.50–1.56 (2H, m), 2.10–2.23 (2H, m), 3.33–3.49 (2H, m), 2.97–3.01 (1H, m), 3.46–3.84 (1H, m), 4.54 (2H, m), 4.94–5.06 (2H, m), 5.77–5.83 (1H, m), 7.27–7.35 (5H, m).
$^{13}$C-NMR (CDCl$_3$, 75.5 MHz) δ : 29.8, 32.3, 69.8, 73.3, 74.4, 114.7, 127.5, 127.6, 128.3, 138.1
IR (neat) V$_{max}$ c$^{-1}$; 3436, 2914, 1639, 1449, 1091, 912, 702.
MS (EI) calcd for C$_{13}$H$_{18}$O$_3$ 206 Found; 206.

Example 2

(2R)-1-Benzyl-2-ethoxyethylpenten-1,2-5-al

To a solution of compound 1 (2.06 g, 10.0 mmole) in dry dichloromethane (100 mL) at 0° C were added dropwise ethyl vinyl ether (1.6 mL, 15.0 mmole) and pyridinium p-toluenesulfonate (250 mg, 10 mol %) and the mixture was stirred at room temperature for 3 h. The reaction was quenched with saturated sodium bicarbonate (50 mL). The organic layer was separated from the aqueous layer and the aqueous layer was extracted with dichloromethane (50 mL). The combined organic extracts were washed with brine, dried over anhydrous magnesium sulfate, and concentrated. The oily residue obtained was used for the next step without further purification. To a solution of the above oily residue (2.78 g, 10.0 mmole) in THF (200 mL) at 0° C. were added N-methylmorpholine N-oxide (1.2 g, 10.0 mmole), OsO$_4$ (0.5 mL, 0.2 M solution in benzene), and water (1.8 mL). The resulting mixture was stirred at room temperature for 30 h and water (100 mL) was added followed by the addition of NaIO$_4$ (6.4 g, 30.0 mmole). After stirring at room temperature for 30 min, the organic layer was separated from the aqueous layer and the aqueous layer was extracted with ethyl ether (100 mL). The combined organic extracts were washed with brine, dried over anhydrous magnesium sulfate, and concentrated using rotatory evaporation. The oily residue was purified by flash column chromatography (hexane/EtOAc=10/1) to yield 2.66 g (95%) of the desired product as a colorless oil.

$^1$H-NMR (CDCl$_3$, 300 MHz) δ: 1.11–1.28 (6H, m), 1.63–1.99 (4H, m), 3.41–3.64 (4H, m), 4.24–4.28 (1H, m), 4.57 (2H, s), 4.72 (1H, q, J=5.4 Hz), 7.27–7.35 (5H, m), 9.74 (1H, m)

Example 3

Ethyl-(E)-(2R)-1-Benzyloxy-2-ethpoxyethyloxy-5-heptenoate

To a suspension of sodium hydride (720 mg, 18.0 mmole) in dry DME (25 mL) at 0° C. was added dropwise triethylphosphonoacetate (3.6 mL, 18.0 mmole) under nitrogen and the mixture was stirred at 0° C. for 30 min. This homogeneous solution was then transferred via a cannula to a solution of the aldehyde 2 (2.52 g, 9.0 mmole) in dry benzene (25 mL) at 0° C. and the resulting mixture was stirred at 0° C. for 1 h and quenched with saturated ammonium chloride (50 mL). The organic layer was separated from the aqueous layer and the aqueous layer was extracted with ethyl ether (2×50 mL). The combined organic extracts were washed with brine, dried over anhydrous magnesium sulfate, and concentrated using rotary evaporation. The oily residue was purified by flash column chromatography (hexane/Et$_2$O=10/1) to yield 3.1 g (99%) of the desired product as a colorless oil.

$^1$H-NMR (CDCl$_3$, 300 MHz) δ: 1.11–1.36 (9H, m), 1.63–1.81 (2H, m), 2.18–2.40 (2H, m), 3.38–3.85 (5H, m), 4.13–4.21 (2H, m), 4.52 (2H, s), 4.72–4.88 (1H, m), 5.80–5.86 (1H, m), 6.90–7.03 (1H, m), 7.27–7.35 (5H, m).
$^{13}$C-NMR (CDCl$_3$, 75.5 MHz) δ: 14.3, 15.3(15.4), 20.5 (20.7), 27.9(28.1), 30.6(30.9), 60.1(60.2), 60.3(60.6), 72.4(72.6), 73.3(73.8), 74.4(74.6), 99.4(99.8), 121.3, 127.4, 127.5, 127.6, 128.2, 128.3, 137.9, 148.5(148.6), 166.4.
IR (neat) V$_{max}$ cm$^{-1}$; 3436, 3010, 2981, 1703, 1204, 915, 748.
MS (E1) calcd for C$_{20}$H$_{30}$O$_5$ 335 Found; 335.

Example 4

(E)-(2R)-1-Benzyloxy-2-ethoxyxyhyloxy-5-heptne-7-ol

To a solution of compound 3 (3.50 g, 10.0 mmole) in dry dichloromethane (250 mL) at −78° C. was added diisobutylaluminum hydride (15 mL, 22.0 mmole, 1.5 M solution in toluene) and the resulting mixture was stirred at −78° C. for 3 h. The reaction was quenched with saturated ammonium chloride (50 mL). The organic layer was separated from the aqueous layer and the aqueous layer was extracted with dichloromethane (100 mL). The combined organic extracts were washed with brine, dried over anhydrous magnesium sulfate, and concentrated using rotatory evaporation. The oily residue was purified by flash column chromatography (hexane/EtOAc=10/1) to yield 3.0 g (99%) of the desired product as a colorless oil.

$^1$H-NMR (CDCl$_3$, 300 MHz) δ: 1.11–1.39 (6H, m), 1.60–1.70 (2H, m), 1.97–2.21 (3H, m), 3.42–3.81 (6H, m), 4.53 (2H, s), 4.74–4.86 (1H, m), 7.27–7.37 (5H, m).
$^{13}$C-NMR (CDCl$_3$, 75.5 MHz) δ: 15.2(15.4), 20.5(20.7), 27.9(28.1), 31.6(32.0), 60.0(60.3), 63.4(63.5), 72.6(72.8), 74.3(74.6), 99.4(99.6), 127.3, 127.4, 127.5, 128.1, 128.2, 129.1, 129.2, 132.2, 132.3, 137.9.
IR (neat) V$_{max\ cm}$−1: 3436, 2981, 2854, 1439, 1370, 1096, 739, 690.
MS (EI) calcd for C$_{18}$H$_{28}$O$_4$—EVE 235 Found; 235.

Example 5

(2S,3S)-Epoxy-6-ethoxyehyloxy-7-benzyloxy-1-heptanol

To a suspension of 4 A molecular sieves (580 mg) in dry dichloromethane (20.0 mL) at −25° C. were added dropwise L-(+)-diisopropyltartrate (0.06 mL, 0.321 mmole), titanium isoproxide (0.043 mL, 0.13 mmole), and tert-butyl hydroperoxide (1.0 mL, 5.2 mmole) under nitrogen. The resulting mixture was stirred at −25° C. for 15 min and then a solution of compound 4 (660 mg, 2.14 mmole) in dry dichloromethane (5.0 mL) was added dropwise. The reaction mixture was stirred at −25° C. for 1 h and then stored in a 25° C. freezer for 24 h. A solution of 10% aqueous tartric acid (25 mL) was then added and the mixture was stirred at 0° C. for 1 h. The organic layer was separated from the aqueous layer and the aqueous layer was extracted with dichloromethane (2×25 mL). The combined organic extracts were washed with brine, dried over anhydrous magnesium sulfate, and concentrated using rotatory evaporation. The oily residue was purified by flash column chromatography (hexane/EtOAc—10/1) to yield 645 mg (93%) of the desired product as a colorless oil.

$^1$H-NMR (CDCl$_3$, 300 MHz) δ: 1.12–1.31 (6H, m), 1.52–1.79 (4H, m), 2.91–2.96 (2H, m), 3.42–3.88 (6H, m), 4.53 (2H, s), 4.74–4.86 (1H, m), 7.27–7.37 (5H, m).
$^{13}$C-NMR (CDCl$_3$, 75.5 MHz) δ: 15.3(15.4), 20.5(20.7), 27.4(27.8), 28.7(30.0), 55.9(56.0), 58.3(58.4), 60.3(60.7), 72.6(72.7), 73.3, 74.3(74.7), 99.5(99.8), 127.4, 127.5, 128.1, 128.2, 137.9.
IR (neat) V$_{max}$cm$^{-1}$: 3440, 2988, 2918, 2875, 1449, 1373, 1061, 749.
MS (EI) calcd for C$_{18}$H$_{28}$O$_5$—EVE 251 Found; 251.

Example 6

2S,3S)-Epoxy-6-ethoxyethyloxy-7-benzyloxy-1-haptanol,p-nitrobenzoate

To a solution of compound 5 (1.09 g, 3.36 mmole) in dry dichloromethane (50 mL) at 0° C. were added triethylamine (0.94 mL, 6.72 mmole) andp-nitrobenzoyl chloride (630 mg, 3.39 mmole) and the resulting mixture was stirred at 0° C. for 1 h. The reaction was quenched with saturated ammonium chloride (50 mL). The organic layer was separated from the aqueous layer and the aqueous layer was extracted with dichloromethane (100 mL). The reaction mixture was concentrated using rotatory evaporation and the oily residue was purified by flash column chromatography (hexane/Et$_2$O=10/1) to yield 1.56 g (98%) of the desired product as a colorless oil.

$^1$H-NMR (CDCl$_3$, 300 MHz) δ: 1.12–1.31 (6H, m), 2.01–2.15 (2H, m), 1.58–1.82 (2H, m), 2.94–3.14 (2H, m), 3.44–4.77 (10H, m), 7.33–7.34 (5H, m), 8.22–8.28 (4H, m).
$^{13}$C-NMR (CDCl$_3$, 75.5 MHz) δ: 15.3(15.4), 20.5(20.7), 27.4(27.8), 28.6(28.9), 55.0(55.1), 56.5(56.6), 60.3(60.7), 65.9(66.0), 72.5(72.6), 73.3, 74.1(74.7), 99.4(99.9), 123.4, 127.4(127.5) 128.2, 130.7, 134.9, 137.9, 164.2.
IR (neat) V$_{max}$cm$^{-1}$: 2980, 2929, 2857, 2355, 1720, 1526, 1270, 1111, 711.

Example 7

THF p-nitrobenzoate

To a solution of compound 6 (500 mg, 1.06 mmole) in methanol (15 mL) was -added Dowex-50 resin (1.0 g) and the resulting mixture was stirred at room temperature for 5 h. The reaction mixture was concentrated using rotary evaporation and the oily residue was purified by flash column chromatography (hexane/EtOAc)=4/1) to yield 382 mg (90%) of the desired product as a colorless oil.

$^1$H-NMR (CDCl$_3$, 300 MHz) δ: 1.69–2.09 (4H, m), 2.73 (1H, bs), 3.46–3.49 (2H, m), 4.09–4.12 (2H, m), 4.24–4.28 (1H, m), 4.34–4.40 (2H, m), 4.56–4.58 (2H, m), 7.33–7.35 (5H, m), 8.22–8.28 (4H, m.

$^{13}$C-NMR (CDCl$_3$, 75.5 MHz) δ: 26.4, 28.5, 70.7, 72.0, 72.7, 73.3, 78.6, 79.3, 123.3, 127.3, 128.2, 128.3, 130.6, 135.0, 137.9, 150.3, 164.6
IR (neat) V$_{max}$cm$^{-1}$: 3241, 2873, 2356, 2335, 1726, 1347, 1291, 871.

Example 8

THF-epoxide

To a solution of compound 7 (1.2 g, 3.0 mmole) in dry dichloromethane (20 mL) at 0° C. were added triethylamine (1.0 mL, 7.2 mmole) and methanesulfonyl chloride (0.28 mL, 3.6 mmole) and the resulting mixture was stirred at 0° C. for 1 h. The reaction was quenched with saturated ammonium chloride (50 mL). The organic layer was separated from the aqueous layer and the aqueous layer was extracted with dichloromethane (2×20 mL). The combined organic extracts were washed with brine, dried over anhydrous magnesium sulfate, and concentrated using rotatory evaporation. The oily residue obtained was used for the next step without further purification. To a solution of the above mesylate in dry methanol (25 mL) at 0° C. was added sodium methoxide (1.62 g, 30.0 mmole) under nitrogen. The reaction mixture was stirred at 0° C. for 30 min and then at room temperature for 1 h. The methanol was removed under reduced pressure and the remaining residue was partitioned between ether (20 mL) and water 20 mL). The organic layer was separated from the aqueous layer and the aqueous layer was extracted with ether (2×25 mL). The combined organic extracts were washed with brine, dried over anhydrous magnesium sulfate, and concentrated using rotatory evaporation. The oily residue was purified by flash column chromatography (hexane/EtOAc=10/1) to yield 593 mg (85%) of the desired product as a colorless oil.
$^1$H-NMR (CDCl$_3$, 300 MHz) δ: 1.67–1.93 (2H, m), 2.01–2.15 (2H, m), 2.68–2.78 (2H, m), 2.97–3.01 (1H, m), 3.46–3.48 (2H, m), 3.94–4.00 (1H, m), 4.18–4.26 (1H, m), 4.57 (1H, s), 7.27–7.35 (51H, m).
$^{13}$C-NMR (CDCl$_3$, 75.5 MHz) d: 28.3, 28.6, 44.0, 54.0, 72.5, 73.2, 78.4, 78.7, 127.3, 127.4, 128.1, 138.1.
IR (neat) V$_{max}$ cm$^{-1}$: 2975, 2863, 1457, 1256, 1088, 886, 752
HRMS EI) calcd for C$_{14}$H$_{18}$O$_3$ 234.1256 Found; 234.1259.

Example 9

THF-aldehyde

To a suspension of copper bromide (110 mg) in dry THF (10 mL) at 0° C. was added dropwise undecyl magnesium bromide (prepared from 10.0 mmole of 1-bromoundecane and 20.0 mmole of magnesium powder in 20 mL of dry ether) under nitrogen and the mixture was stirred at 0° C for 5 min. A solution of TH-epoxide 8 (300 mg, 1.28 mmole) was added dropwise and the resulting mixture was stirred at 0° C. for 30 min and quenched with saturated ammonium chloride (25 mL). The layers were separated and the aqueous layer was extracted with ether (2×25 mL). The combined organic extracts were washed with brine, dried over anhydrous magnesium sulfate, and concentrated using rotatory evaporation. The oily residue was purified by flash column chromatography (hexane/EtOAc=10/1) to yield 440 mg (85%) of the epoxide-opening product as a colorless oil. This material (1.0 mmole) was then dissolved in dry dichloromethane (15 mL) and cooled down to 0° C. N,I-diisopropylethylamine (0.87 mL, 5.0 mmole) and chloromethyl methyl ether (0.15 mL, 2.0 mmole) were added and the resulting mixture was stirred at room temperature for 24 h. The reaction mixture was concentrated using rotatory evaporation and the oily residue was purified by flash column chromatography (hexane/EtOAc=8/1) to yield 439 mg (98%) of the desired protected alcohol as a colorless oil. A solution of the protected product (468 mg, 1.04 mmole) in EtOAc (25 mL) containing palladium on activated carbon (catalytic amount) was subjected to hydrogenation for 12 h at room temperature. The catalyst was filtered and the solvent was removed under reduced pressure to provide the debenzylation product quantitatively. To a solution of oxalyl chloride (0.055 mL, 0.3 mmole) in dry dichloromethane (3.0 mL) at −78° C. was added dry DMSO (0.068 mL, 0.96 mmole) and the mixture was stirred at this temperature for 2 min under nitrogen. A solution of the debenzylation product (22 mg, 0.06 mmole) in dry dichloromethane (1.5 mL) was added and the resulting mixture was stirred at −78° C. for 30 min. Triethylamine (0.133 mL, 0.96 mmole) was added and the layers were separated. The aqueous layer was extracted with ether (2×5 mL) and the combined organic extracts were washed with brine, dried over anhydrous magnesium sulfate, and concentrated using rotatory evaporation. The oily residue was purified by flash column chromatography (hexane/EtOAc=10/1) to yield 19 mg (85%) of the desired product as a colorless oil which decomposes slowly at room temperature and should be used immediately.
$^1$-NMR (CDCl$_3$, 300 MHz) δ: 0.88 (3H, t, J=6.6 Hz), 1.20–2.22 (26H, m), 3.42 (3H, 3), 3.51–3.57 (1H, m), 4.10–4.17 (1H, m), 4.32–4.37 (1H, m), 4.71 (1H, d, J=6.9 Hz), 4.80 (1H, d, J=6.6 Hz), 9.67 (1H, d, J=1.8 Hz).

Example 10

THF-phenylsulfone

To a solution of methyl phenyl sulfone (470 mg, 3.0 mmole) in dry THF (10.0 mL) at −78° C. was dropwise added n-BuLi (1.2 mL, 3.0 mmole, 2.5 M solution in hexanes) under nitrogen and the resulting mixture was stirred at this temperature for 30 min followed by the addition of boron trifluoride diethyl etherate (0.092 mL, 1.0 mmole). A solution of the THR-epoxide (234 mg, 1.0 mmole) in dry THF (5.0 mL) was added and the resulting mixture was stirred at −78° C. for 3 h and quenched with saturated ammonium chloride (5.0 mL). The product was extracted with EtOAc (3×20 mL) and the combined organic extracts were washed with brine, dried over anhydrous magnesium sulfate, and concentrated using rotatory evaporation. The oily residue was purified by flash column chromatography (hexane/EtOAc=1/1) to yield 370 mg (95%) of the desired product as a colorless oil. This material (307 mg, 0.787 mmole) was then dissolved in dry dichloromethane (15 mL) and cooled down to 0° C. N-N-diisopropylethylamine (0.82 mL, 4.7 mmole) and chloromethyl methyl ether (0.15 mL, 2.0 mmole) were added and the resulting mixture was stirred at room temperature for 24 h. The reaction mixture was concentrated using rotary evaporation and the oily residue was purified by flash column chromatography (hexane/EtOAc=2/1) to yield 325 mg (95%) of the desired protected alcohol as a colorless oil.
$^1$H-NMR (CDCl$_3$, 300 MHz) δ: 1.58–2.07 (8H, m), 3.23–3.35 (2H, m), 3.30 (3H, s), 3.44 (2H, d, J=4.8 Hz), 3.55–3.61 (1H, m), 3.95–4.02 (1H, m), 4.10–4.16 (1H, m), 4.55 (2H, s), 4.59 (1H, d, J=7.2 Hz), 4.72 (1H, d, J=6.9 Hz), 7.26–7.93 (10H, m).
$^{13}$C-NMR (CDCl$_3$, 75.5 MHz) δ: 24.5, 27.8, 28.4, 52.6, 55.7, 72.5, 73.1, 77.8, 78.2, 80.9, 96.8, 127.2, 127.3, 127.8, 128.1, 129.0, 133.4, 138.1, 138.8.
IR (neat) V$_{max}$ cm$^{-1}$: 2928, 2892, 2356, 2338, 1447, 1308, 1146, 1031, 917, 748, 694.

We claim:

1. A stereoisomeric compound of the formula

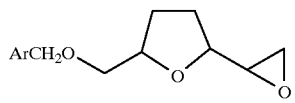

wherein Ar is phenyl or substituted phenyl.

2. The compound of claim 1, wherein Ar is phenyl substituted by lower alkyl, lower alkoxy, halo or nitro.

3. The compound of claim 1, wherein Ar is phenyl.

4. A stereoisomeric compound of the formula

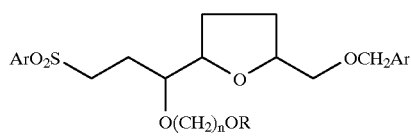

wherein Ar is phenyl or substituted phenyl; R is lower alkyl, and n is 1 or 2.

5. The compound of claim 4, wherein Ar is phenyl substituted by lower alkyl, lower alkoxy, halo or nitro.

6. The compound of claim 4, wherein Ar is phenyl.

7. The compound of claim 4, wherein R is methyl.

8. The compound of claim 4, wherein Ar is phenyl, R is methyl and n is 1.

9. A process for preparing a stereoisomeric compound of the formula

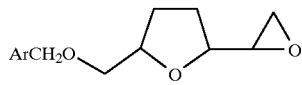

wherein Ar is phenyl or substituted phenyl comprising the steps of:

(a) reacting a stereoisomeric compound of the formula

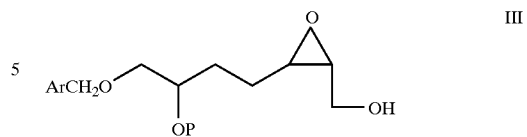

wherein P is an acid labile protecting group, with an aromatic carboxylic acid halide or anhydride, or an aromatic sulfonyl halide to form a stereoisomeric compound of the formula

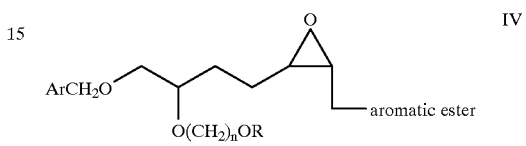

(b) reacting the resulting aromatic ester of formula IV with an acidic resin in an alcohol solvent to afford a stereoisomeric compound of the formula

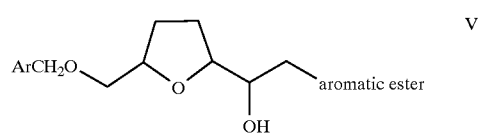

(c) reacting the product of step (b) of formula V with methane sulfonyl halide or an arylsulfonyl halide followed by an alkali metal alkoxide or carbonate in an alcohol solvent to afford the stereoisometric product of the above formula I.

10. The process of claim 9, wherein the aromatic acid chloride in step (a) or anhydride is p-nitrobenzoyl chloride or anhydride.

11. The process of claim 9, wherein in step (a) P is 1-ethoxyethyl.

12. The process of claim 9, wherein in step (c), the methane sulfonyl halide is methane sulfonyl chloride, and the arylsulfonyl halide is p-toluenesulfonyl chloride.

13. The process of claim 9, wherein in step (c) the alkali metal alkoxide is sodium methoxide, the alkali metal carbonate is potassium carbonate and the alcohol is methanol.

* * * * *

UNITED STATES PATENT AND TRADEMARK OFFICE
CERTIFICATE OF CORRECTION

PATENT NO.   : 5,914,410
DATED        : June 22, 1999
INVENTOR(S)  : Li et al.

It is certified that error appears in the above-identified patent and that said Letters Patent is hereby corrected as shown below:

Column 1,
Line 41, "180 1" should read -- 1801 --

Column 4,
Line 22, "Wittig-Homer" should read -- Wittig-Horner --

Column 9,
Scheme 5, #22, insert -- TBDMSO -- under the left lower "▲"
Scheme 5, #24, insert diagram #24 after diagrams #22 and #23 and before Scheme 6 as follows:

--
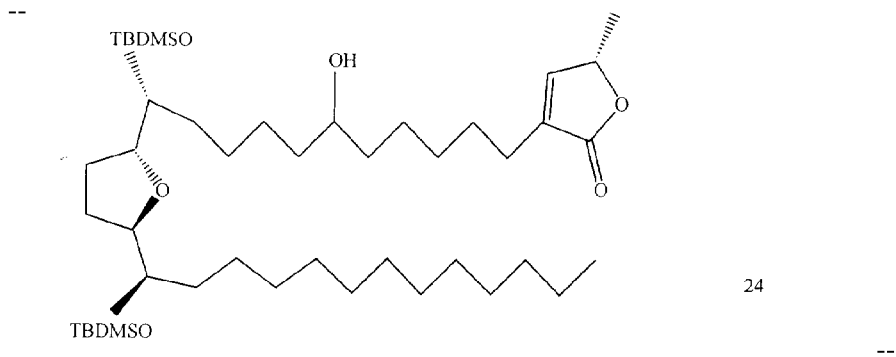
--

Column 10,
Line 6, #23, insert -- TBDMSO -- under the left lower "▲"

Column 12,
Line 15, "TEF" should read -- THF --
Line 32, "$^{v}mzx^{c-1}$," should read -- $^{v}max^{cm-1}$; --
Line 37, "1,2-5-al" should read -- 1,2-diol-5-al --

Column 13,
Line 3, "ethpoxyethyloxy" should read -- ethoxyethyloxy --
Line 36, "ethoxyxyhyloxy" should read -- ethoxyethyloxy --
Line 63, "ethoxyehyloxy" should read -- ethoxyethyloxy --

UNITED STATES PATENT AND TRADEMARK OFFICE
CERTIFICATE OF CORRECTION

PATENT NO. : 5,914,410
DATED : June 22, 1999
INVENTOR(S) : Li et al.

It is certified that error appears in the above-identified patent and that said Letters Patent is hereby corrected as shown below:

Column 14,
Line 31, "haptanol" should read -- heptanol --
Line 67, "(4H,m." should read -- (4H,m). --

Column 15,
Line 38, "(51H,m)." should read -- (5H,m). --

Column 16,
Line 26, "$^1$-NMR" should read -- $^1$H-NMR --
Line 39, "THR" should read -- THF --

Signed and Sealed this

Twenty-fourth Day of September, 2002

Attest:

JAMES E. ROGAN
Attesting Officer — Director of the United States Patent and Trademark Office